(12) United States Patent
Mekhail et al.

(10) Patent No.: US 9,084,636 B2
(45) Date of Patent: Jul. 21, 2015

(54) SURGICAL PLATE SYSTEM AND METHOD

(75) Inventors: Anis Mekhail, Willow Spring, IL (US);
Steven E. Mather, Hinsdale, IL (US);
Thibaut Guffroy, Westchester, IL (US);
Wagdy W. Asaad, Burr Ridge, IL (US)

(73) Assignee: Spine Craft, LLC, Westmont, IL (US)

( * ) Notice: Subject to any disclaimer, the term of this patent is extended or adjusted under 35 U.S.C. 154(b) by 462 days.

(21) Appl. No.: 12/987,590

(22) Filed: Jan. 10, 2011

(65) Prior Publication Data
US 2012/0179207 A1 Jul. 12, 2012

(51) Int. Cl.
*A61B 17/80* (2006.01)
*A61B 17/86* (2006.01)
*A61B 17/70* (2006.01)
*A61B 17/88* (2006.01)

(52) U.S. Cl.
CPC ......... *A61B 17/7059* (2013.01); *A61B 17/8038* (2013.01); *A61B 17/8052* (2013.01); *A61B 17/8605* (2013.01); *A61B 17/8685* (2013.01); *A61B 17/8877* (2013.01)

(58) Field of Classification Search
CPC ........... A61B 17/7059; A61B 17/8038; A61B 17/8052
USPC .......................... 606/286–291, 293, 305, 307
See application file for complete search history.

(56) References Cited

U.S. PATENT DOCUMENTS

| | | | |
|---|---|---|---|
| 6,117,173 A * | 9/2000 | Taddia et al. | 623/16.11 |
| 6,235,033 B1 * | 5/2001 | Brace et al. | 606/288 |
| 6,488,681 B2 | 12/2002 | Martin et al. | |
| 6,554,834 B1 | 4/2003 | Crozet et al. | |
| 6,613,053 B1 * | 9/2003 | Collins et al. | 606/293 |
| 6,669,700 B1 * | 12/2003 | Farris et al. | 606/287 |
| 6,858,030 B2 | 2/2005 | Martin et al. | |
| 6,974,460 B2 | 12/2005 | Carbone et al. | |
| 7,166,111 B2 * | 1/2007 | Kolb et al. | 606/96 |
| 7,691,133 B2 * | 4/2010 | Partin et al. | 606/289 |
| 7,736,380 B2 * | 6/2010 | Johnston et al. | 606/280 |
| 7,758,620 B2 * | 7/2010 | Porcher | 606/290 |
| 7,931,678 B2 * | 4/2011 | Konieczynski et al. | 606/280 |
| 7,935,137 B2 * | 5/2011 | Gorhan et al. | 606/301 |
| 8,075,602 B2 * | 12/2011 | Lombardo et al. | 606/290 |
| 8,282,675 B2 * | 10/2012 | Maguire et al. | 606/289 |
| 8,287,575 B2 * | 10/2012 | Murner et al. | 606/287 |
| 8,652,183 B1 * | 2/2014 | Truman | 606/305 |
| 2003/0055426 A1 | 3/2003 | Carbone et al. | |
| 2003/0105462 A1 * | 6/2003 | Haider | 606/69 |

(Continued)

*Primary Examiner* — Matthew Lawson
*Assistant Examiner* — Zade Coley
(74) *Attorney, Agent, or Firm* — Alan W. Cannon; Law Office of Alan W. Cannon

(57) ABSTRACT

A surgical plate system, components and methods of using are described. A surgical plate system includes a plate having an anterior surface, a posterior surface, a longitudinal axis, a transverse axis and a through hole passing through the anterior and posterior surfaces. A variable fastener is configured and dimensioned to connect to the plate, the variable fastener having a head and a shaft extending distally from the head. The head is configured to assume different proximal end diameters. The head, in a first configuration allows inward flexing to reduce a diameter of the head to allow the head to pass through an entrance opening of the through hole. In a second configuration, the head is prevented from flexing inwardly thereby preventing the head from backing out of the entrance opening, while allowing articulation of the head, within the through hole, relative to the plate.

14 Claims, 11 Drawing Sheets

(56) References Cited

U.S. PATENT DOCUMENTS

| | | | |
|---|---|---|---|
| 2003/0171753 A1* | 9/2003 | Collins et al. | 606/69 |
| 2003/0171754 A1* | 9/2003 | Del Medico | 606/69 |
| 2003/0225409 A1* | 12/2003 | Freid et al. | 606/69 |
| 2004/0030336 A1 | 2/2004 | Khanna | |
| 2004/0127896 A1* | 7/2004 | Lombardo et al. | 606/61 |
| 2004/0220570 A1 | 11/2004 | Frigg | |
| 2004/0243126 A1 | 12/2004 | Carbone et al. | |
| 2005/0228386 A1* | 10/2005 | Ziolo et al. | 606/69 |
| 2005/0251137 A1* | 11/2005 | Ball | 606/61 |
| 2006/0122602 A1* | 6/2006 | Konieczynski et al. | 606/69 |
| 2006/0122604 A1* | 6/2006 | Gorhan et al. | 606/69 |
| 2006/0149251 A1* | 7/2006 | Ziolo et al. | 606/69 |
| 2006/0167456 A1* | 7/2006 | Johnston et al. | 606/69 |
| 2006/0200147 A1* | 9/2006 | Ensign et al. | 606/69 |
| 2006/0264936 A1* | 11/2006 | Partin et al. | 606/61 |
| 2007/0225717 A1 | 9/2007 | Hawkes | |
| 2008/0132953 A1 | 6/2008 | Carbone et al. | |
| 2008/0161862 A1 | 7/2008 | Ensign | |
| 2008/0221691 A1 | 9/2008 | Chaput et al. | |
| 2008/0281359 A1 | 11/2008 | Abdou | |
| 2008/0288000 A1* | 11/2008 | Cawley | 606/291 |
| 2009/0012571 A1* | 1/2009 | Perrow et al. | 606/280 |
| 2009/0062862 A1* | 3/2009 | Perrow et al. | 606/280 |
| 2009/0192553 A1* | 7/2009 | Maguire et al. | 606/305 |
| 2009/0216282 A1* | 8/2009 | Blake et al. | 606/286 |
| 2009/0270927 A1* | 10/2009 | Perrow et al. | 606/286 |
| 2010/0087878 A1 | 4/2010 | Abdou | |
| 2010/0160973 A1* | 6/2010 | Leung | 606/289 |
| 2010/0211116 A1* | 8/2010 | Suh et al. | 606/305 |
| 2010/0256686 A1* | 10/2010 | Fisher et al. | 606/286 |

* cited by examiner

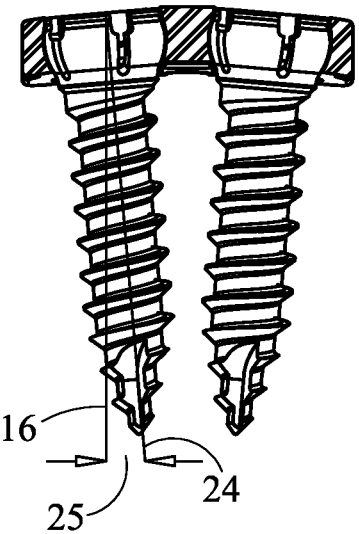
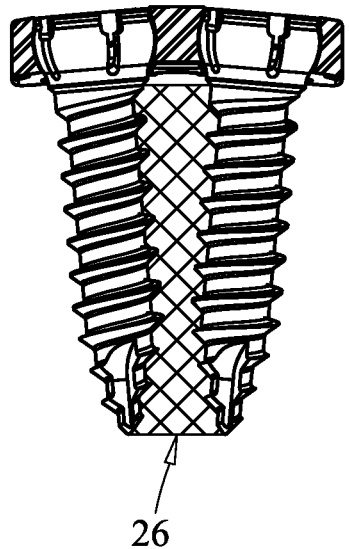
FIG. 5A   FIG. 5B
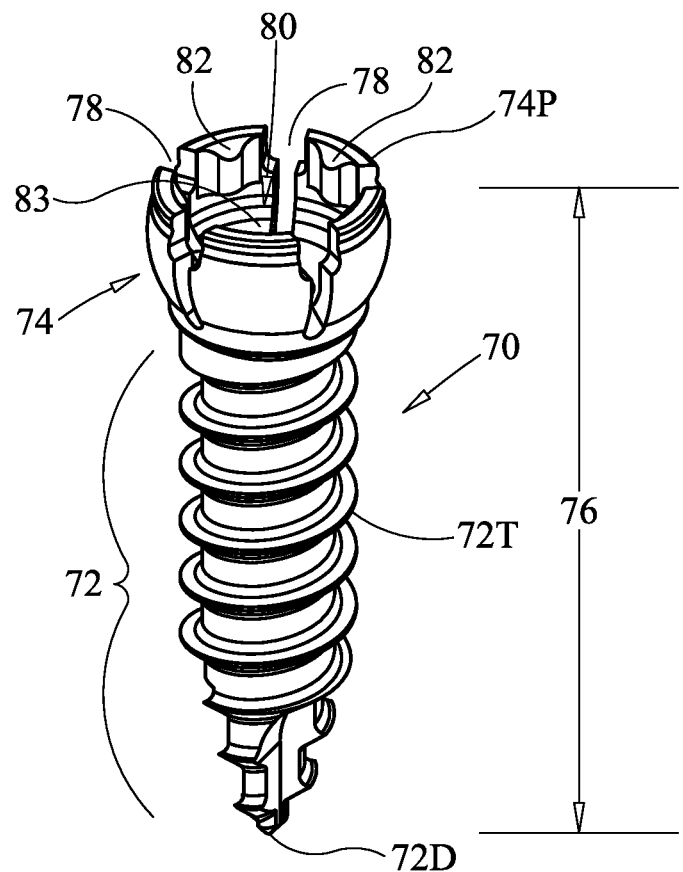
FIG. 6

SURGICAL PLATE SYSTEM AND METHOD

BACKGROUND OF THE INVENTION

Back pain can be caused by a variety of factors, including, but not limited to the rupture or degeneration of one or more intervertebral discs due to degenerative disk disease, spondylolisthesis, deformative disorders, trauma, tumors and the like. In such causes, pain typically results from compression or irritation of spinal nerve roots by reduced spacing between adjacent vertebrae, a damaged disk and/or misalignment of the spine resulting from the injury or degeneration.

Common forms of treating such pain include various types of surgical procedures that include mounting a plate across two or more adjacent vertebrae to stabilize them, including, but not limited to aligning the vertebrae to alleviate pain and achieve bony fusion between the aligned vertebrae. After installation of such a plate, once the patient has recovered to the extent where the patient can at least sit upright, the gravitational forces on the spine typically cause some subsidence forces to be applied to the treated vertebrae, particularly in cases where one or more grafts have been placed between one or more pairs of adjacent vertebrae. Inadequate grafting techniques, poor graft quality and or poor bone quality (e.g., osteoporosis) are factors that can further exacerbate the amount of subsidence that occurs.

Current plate systems do not provide a screw-plate interface that is adequate to account for the subsidence that occurs. Specifically, current systems do not allow sufficient angulation of the screws relative to the plane of the plate to allow the screws to be oriented as needed during the initial anchoring of the plate to the vertebrae. Further, many current systems do not allow angular movement of the screws relative to the longitudinal axis of the plate to further accommodate subsidence.

There is a continuing need for plates and plate systems that allow improved angulation of screws relative to the face or plane of the plate. There is a continuing need for plates and plates systems that include dynamic features that allow for angular changes in positioning of one or more screws relative to the longitudinal axis or length dimension of the plate that they are installed through, to dynamically accommodate subsidence. The present invention meets at least all of the above needs.

SUMMARY OF THE INVENTION

In one aspect of the present invention, a surgical plate system is provided that includes: a plate having an anterior surface, a posterior surface, a longitudinal axis, a transverse axis and a through hole passing through the anterior and posterior surfaces; and a variable fastener configured and dimensioned to connect to the plate, the variable fastener comprising a head and a shaft extending distally from the head, wherein the head is configured to assume different proximal end diameters, and wherein the head, in a first configuration allows inward flexing to reduce a diameter of the head to allow the head to pass through an entrance opening of the through hole, and wherein in a second configuration, the head is prevented from flexing inwardly thereby preventing the head from backing out of the entrance opening, while allowing articulation of the head, within the through hole, relative to the plate.

In at least one embodiment, the plate comprises a fixed fastener configured and dimensioned to connect to the plate, the fixed fastener comprising a second head and a second shaft extending distally from the second head, wherein the second head is configured to assume different proximal end diameters, and wherein the second head, in a first configuration allows inward flexing to reduce a diameter of the second head to allow the second head to pass through the entrance opening of the through hole, and wherein in a second configuration, the second head is flexed outwardly, thereby preventing the second head from backing out of the entrance opening and also compressing the second head against inner side walls of the plate surrounding the opening, thereby preventing articulation of the second head, within the through hole, relative to the plate.

In at least one embodiment, the plate comprises a pair of the openings arranged side by the along a direction of the transverse axis: a first opening of the pair having a first axis defining a direction in which the first opening extends from the anterior face to the posterior face, and a second opening of the pair having a second axis defining a direction in which the second opening extends from the anterior face to the posterior face, wherein the first and second axes are medially inclined towards one another, such that the first and second axes converge toward one another in a direction from the anterior surface to the posterior surface.

In at least one embodiment, the plate comprises two openings, a first of the opening being formed nearer a first end of the plate, and a second of the openings being formed nearer a second end of the plate, wherein the first opening is configured to allow angulation of the fastener relative to a perpendicular to the longitudinal axis in a direction from the anterior surface to the posterior surface, by a first angle toward the first end, and by a second angle toward the second end, wherein the first angle is greater than the second angle.

In at least one embodiment, the second opening is configured to allow angulation of the fastener relative to the perpendicular to the longitudinal axis in a direction from the anterior surface to the posterior surface, by a third angle toward the second end, and by a fourth angle toward the first end, wherein the third angle is greater than the fourth angle.

In at least one embodiment, a third opening is formed intermediate of the first and second openings along a direction of the longitudinal axis; wherein the third opening is configured to allow angulation of the fastener relative to the perpendicular to the longitudinal axis in a direction from the anterior surface to the posterior surface, by a third angle toward the first end, and by a fourth angle toward the second end, wherein the third and fourth angles are substantially equal, wherein the first angle is greater than the third angle, and wherein the second angle is less than the fourth angle.

In at least one embodiment, the variable fastener is provided with a variable cam that interacts with a protrusion on an inner surface of the head, wherein in the first configuration, the protrusion is separated from a portion of the cam by a first distance that allows the inward flexing sufficient to reduce the diameter of the head to allow the head to pass through the entrance opening of the through hole, and wherein in the second configuration, the protrusion of the head engages a notch in the cam, thereby preventing the head from flexing inwardly and preventing the head from backing out of the entrance opening.

In at least one embodiment, the fixed fastener is provided with a fixing cam that interacts with a protrusion on an inner surface of the second head, wherein in the first configuration, the protrusion is separated from a portion of the fixing cam by a first distance that allows the inward flexing sufficient to reduce the diameter of the second head to allow the second head to pass through the entrance opening of the through hole, and wherein the fixing cam has a lobe with a progressively increasing radius, whereby rotation of the fixing cam engages the lobe with the protrusion of the second head, first preventing inward flexing of the second head and, with increasing rotation of the cam, flexing the head outward to compress against the inner walls of the through hold, thereby preventing the articulation.

In another aspect of the present invention, a surgical plate system is provided that includes: a plate having an anterior surface, a posterior surface, a longitudinal axis, a transverse axis and a through hole passing through the anterior and posterior surfaces; an entrance opening having a first diameter defined by the through hole in the anterior surface, an exit opening having a second diameter defined by the through hole in the posterior surface, and the through hole having a third diameter intermediate of the entrance and exit openings, wherein the third diameter is greater than the first diameter; and a fastener configured and dimensioned to connect to the plate, the fastener comprising a head and a shaft integral with and extending distally from the head, wherein the head is configured to assume different proximal end diameters, and wherein the head, in a first configuration allows inward flexing to reduce a diameter of the head to allow the head to pass through the entrance opening, and wherein in a second configuration, the head is prevented from flexing inwardly thereby preventing the head from backing out of the entrance opening.

In at least one embodiment, the fastener is a variable fastener comprising a variable cam inserted in the head, and wherein in the second configuration, the head is allowed to articulate within the through hole, relative to the plate.

In at least one embodiment, the fastener is a fixed fastener comprising a fixing cam inserted in the head, and wherein in the second configuration, the head is compressed against inner walls of the plate defining the through hole, thereby preventing articulation of the head relative to the plate.

In another aspect of the present invention, a variable fastener is provided that is adapted for use in a surgical plate system, the fastener including: a head and a shaft extending distally from the head, wherein the head is configured to assume different proximal end diameters, and wherein the head, in a first configuration allows inward flexing to reduce a diameter of the head to a first diameter allowing the head to pass through an entrance opening having a second diameter larger than the first diameter, and wherein in a second configuration, the head is prevented from flexing inwardly and has a third diameter larger than the second diameter, thereby preventing the head from backing out of the entrance opening.

In at least one embodiment, a variable cam interacts with a protrusion on an inner surface of the head, wherein in the first configuration, the protrusion is separated from a portion of the cam by a first distance that allows the inward flexing sufficient to reduce the diameter of the head to the first diameter, and wherein in the second configuration, the protrusion of the head engages a notch in the cam, thereby preventing the head from flexing inwardly and maintaining the head to have the third diameter.

In another aspect of the present invention, an instrument for installation of a fastener during a surgical procedure is provided, the instrument including: a first shaft having a first end effector configured to engage with the fastener to torque the fastener into an intended target: a second shaft coaxial with and rotatable relative to the first shaft, the second shaft having a second end effector configured to engage a locking mechanism to torque the locking mechanism and prevent backout of the fastener from the intended target.

In at least one embodiment, the second shaft is slidable relative to the first shaft and is biased toward a distal end of the first shaft.

In at least one embodiment, the second end effector comprises a plurality of protrusions spaced about a circumference and configured to engage a cam within a head of the fastener.

In at least one embodiment, the instrument includes a first handle fixed to the first shaft and useable to torque the fastener into the intended target, and a second handle fixed to the second shaft and used to torque the locking mechanism, wherein during torqueing of the locking mechanism, the first handle is useable to provide counter-torque to the fastener to prevent further torqueing on the fastener.

In another aspect of the present invention, a method of attaching a plate system to a patient is provided, including: providing a plate having an anterior surface, a posterior surface, a longitudinal axis, a transverse axis, first and second through holes, each the through hole passing through the anterior and posterior surfaces: first and second fasteners configured to pass through the first and second through holes and fasten the plate to the patient: fastening the first and second fasteners through the first and second through holes, respectively, thereby drawing the plate up against the patient, wherein a first head of the first fastener is positioned within the first through hole and a second head of the second fastener is positioned with the second through hole: andactuating a first mechanism in the first head and a second mechanism in the second head to prevent the ability of the first and second heads to flex inwardly in order to back out of the first and second through holes, respectively: wherein at least one of the first and second mechanisms is a variable mechanism that prevents backout of the first or second head, but permits the first or second head to articulate within the first or second through hole, respectively.

In at least one embodiment, the plate is fixed to a spine of the patient, the first fastener is fixed to a first vertebra and the second fastener is fixed to a second vertebra.

In at least one embodiment, at least one of the first and second mechanisms is a fixing mechanism that prevents backout of the first or second head, and also compresses the first or second head against inner walls surrounding the first or second through hole, thereby preventing articulation of the first or second head within the first or second through hole, respectively.

In at least one embodiment, the articulation of the head within the through hole allows variation in an angle of insertion of the fastener through the plate, thereby allowing subsidence of the first vertebra toward the second vertebra.

These and other features of the invention will become apparent to those persons skilled in the art upon reading the details of the systems, components, instruments and methods as more fully described below.

BRIEF DESCRIPTION OF THE DRAWINGS

FIGS. 5A-5B illustrate end views of the system of FIG. 1 viewed facing the left end of the system of FIG. 1

FIG. 6 is a perspective view of a fastener prior to installation of an insert according to an embodiment of the present invention.

DETAILED DESCRIPTION OF THE INVENTION

Figure 1:
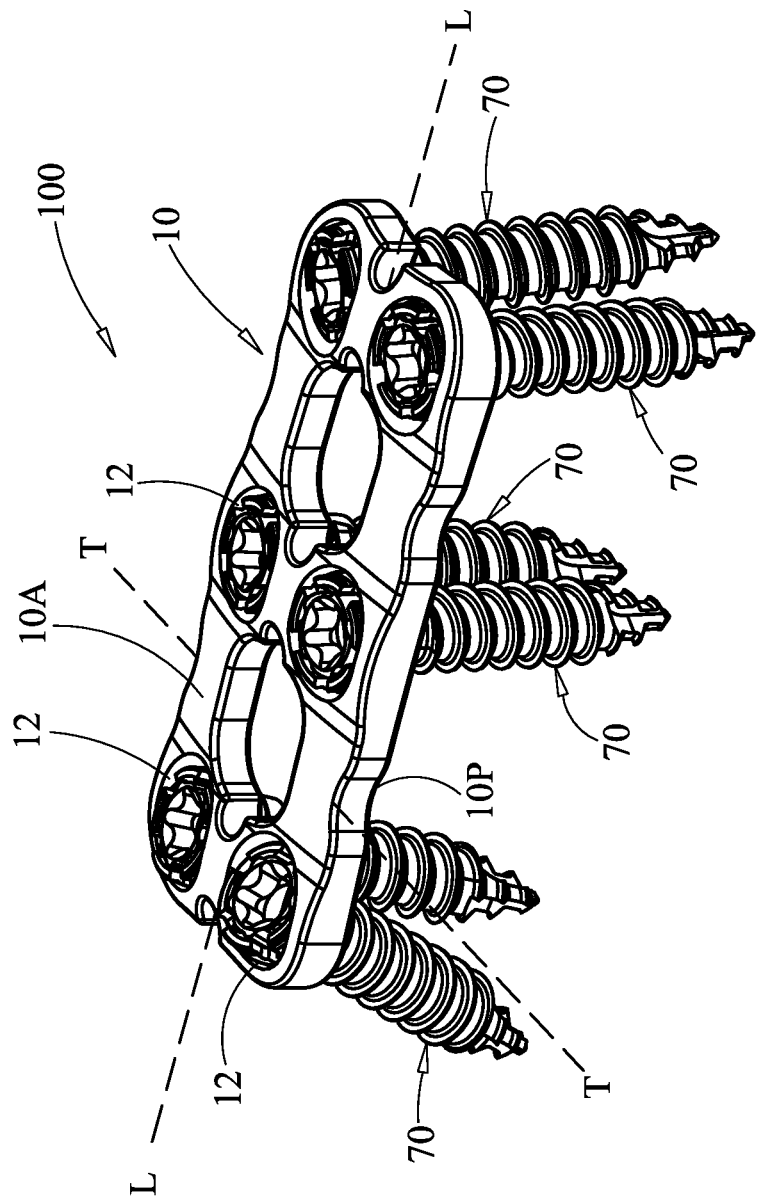
FIG. 1 shows a perspective view of a surgical plate system according to an embodiment of the present invention.

Before the present systems, components and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a screw" includes a plurality of such screws and reference to "the vertebra" includes reference to one or more vertebrae and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A "fixed screw" or "fixed fastener", as used herein, refers to a screw or fastener that is designed not to pivot relative to a plate through which it is inserted, upon completion of installation of the fastener/screw and plate.

A "variable screw" or "variable fastener", as used herein, refers to a screw or fastener that is designed to pivot relative to a plate through which it is inserted, even upon completion of installation of the fastener/screw and plate.

DESCRIPTION

Referring now to FIG. 1, a perspective view of a surgical plate system 100 according to an embodiment of the present invention is shown. System 100 includes bone plate 10 having an anterior surface 10A, a posterior surface 10P, a longitudinal axis L-L and a transverse axis T-T. Fasteners 70 have been installed through each of openings 12 of plate 10 to function in manners described in detail below. Note that FIG. 1 is for illustrative purposes only, and that fasteners 70 are not typically installed through openings 12 prior to placement of the plate 10 against a target site to which it is to be fixed. Each opening 12 is a through hole passing continuously through the plate 10, including the anterior 10A and posterior 10P surfaces.

Figure 2:
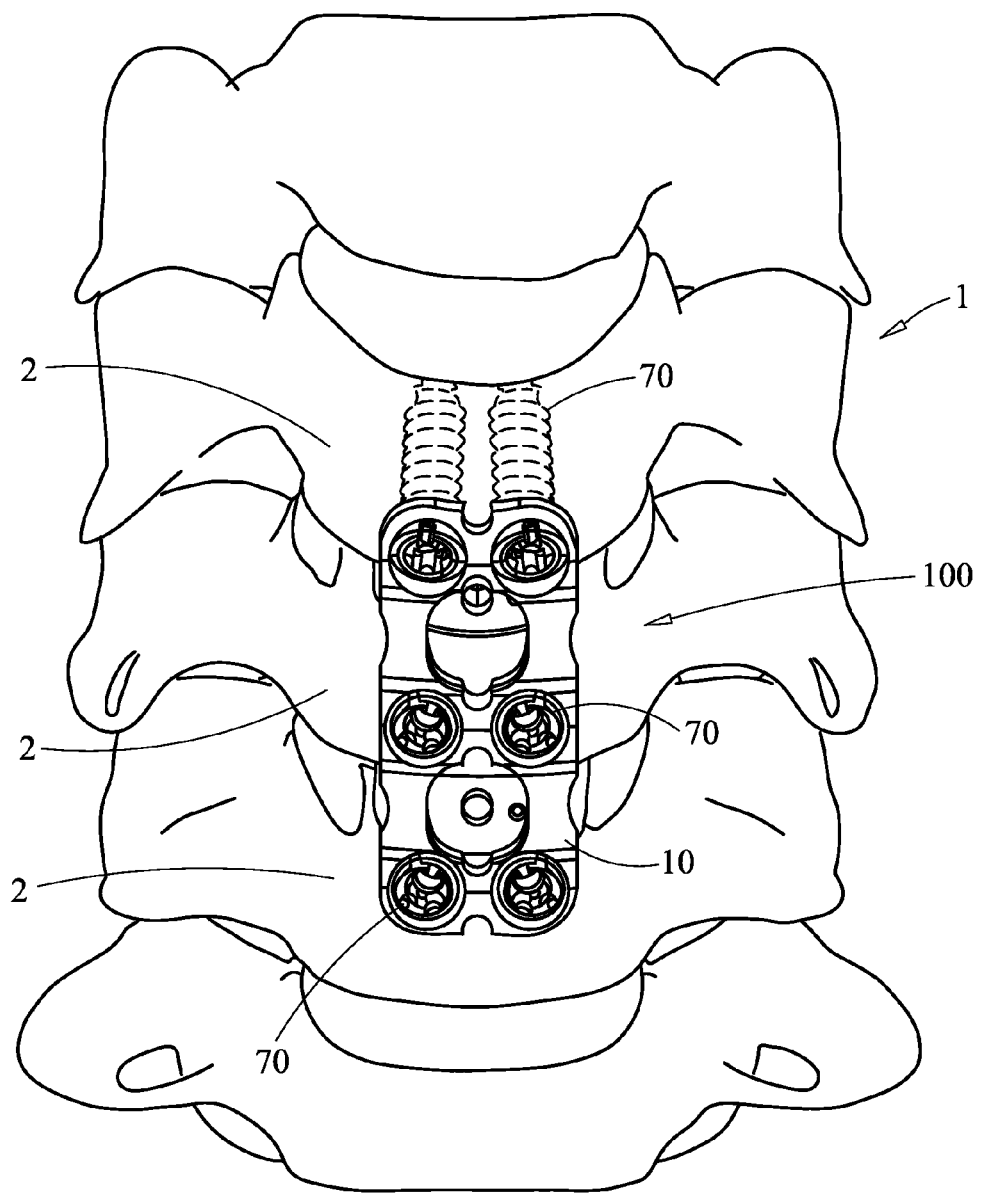
FIG. 2 illustrates an example where fasteners have been screwed into three adjacent vertebrae to mount a plate to the anterior surfaces thereof to perform anterior interbody fusion according to an embodiment of the present invention.
Figure 3A:
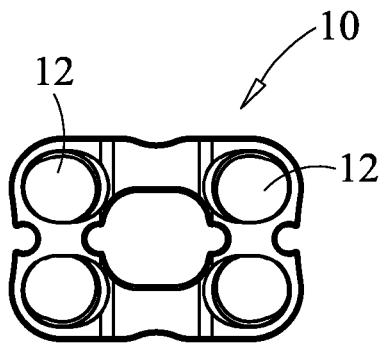
FIG. 3A is a view of a plate for connecting two vertebrae or bone portions according to an embodiment of the present invention.
Figure 3B:
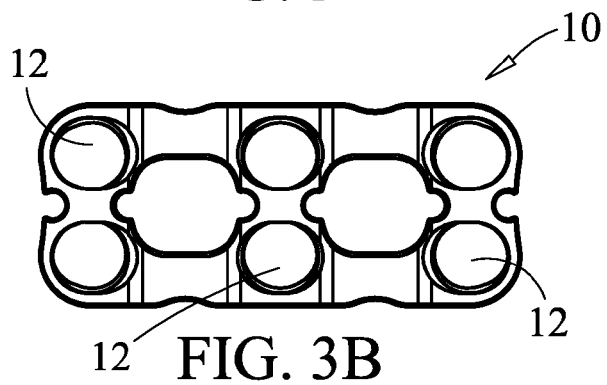
FIG. 3B is a view of a plate for connecting three vertebrae or bone portions according to an embodiment of the present invention.
Figure 3C:
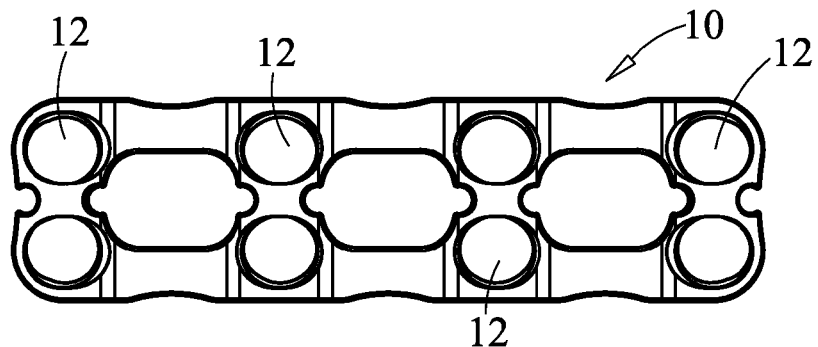
FIG. 3C is a view of a plate for connecting four vertebrae or bone portions according to an embodiment of the present invention.
Figure 3D:
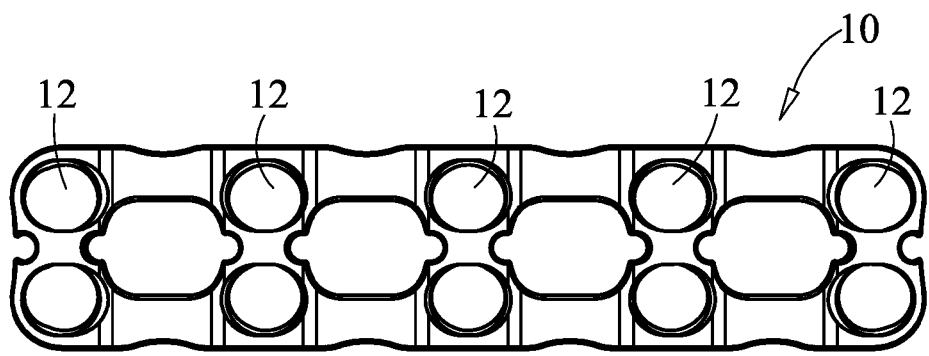
FIG. 3D is a view of a plate for connecting live vertebrae or bone portions according to an embodiment of the present invention.

FIG. 2 illustrates system 100 having been installed on the anterior side of a spinal column 1. It is noted that although this is the preferred method of using the system 100 as described, that system 100 could alternatively be installed on other sides of the spinal column, or across fractures of other bones such as the pelvis or long bones, for example. As one more particular example, the present invention may be used for attachment to the lateral thoracolumbar spine. In the embodiment shown in FIG. 2, fasteners 70 have been screwed into three adjacent vertebrae 2 to mount plate 10 to the anterior surfaces thereof to perform anterior interbody fusion. In the embodiment shown, the plate is installed on cervical vertebrae to perform anterior cervical interbody fusion (ACIF). Installation of the system 100 as described in more detail below, enhances the biomechanical stability of the motion segment of the spine that it is installed on. Additionally, system 100 can provide resistance to graft displacement in instances where grafts are provided between two or more vertebrae 2 to which plate 10 is installed and/or improve the stability of cages or other implants installed intervertebrally. Still further, system 100 provides for a reduced incidence of pseudoarthrosis related to micro motion at the graft-vertebral body interface. System 100 functions to maintain anterior alignment of the vertebrae 2 to which it is mounted when multi-level discectomies or corpectomies are performed. System 100 provides for a decrease in the need to rely upon prolonged external bracing of the spine.

FIGS. 3A-3D are anterior views of embodiment of plates 10 adapted for installation to two to five bone portions (e.g. two to five vertebrae 2), respectively. In the embodiments shown in FIGS. 3A-3D, openings/through holes 12 are arranged side-by-side in pairs along the direction of the transverse axis T-T, two for each bone portion. Other arrangements are also within the scope of the present disclosures. For example, one through hole 12 for each bone portion may be provided, or more than through holes 12 for each bone portion may be provided, or an alternating pattern of two through holes 12, one through hole 12, two through holes 12, . . . etc. may be provided so that two fasteners 70 are installed in alternating bone portions, with only one fastener 70 installed in each intervening bone portions. The present invention is not limited to the specific arrangements just described, as other through hole patterns may alternatively be provided.

Plate 10 can be shaped to conform to the bone portions 2 and have a curvature in one or two directions defined by the longitudinal axis L-L and the transverse axis T-T. Additionally, the plate 10 can have a different shape than those shown and can also be planar.

Each through hole 12 defines an inner surface 14 (see FIG. 4A), which may be spherical. Optionally, the through holes 12 nearest the ends of the plate 10 may be formed on the anterior surface 10A to be oval (see FIG. 4B) so that the fastener inserted therein has a greater range of angularity in the direction aligned with the longitudinal axis L-L of the plate 10 (cepahlad-caudal direction when the plate is installed on the spinal column). The through holes 12 intermediate of the holes 12 nearest the ends can be formed as a circular shape on the anterior face 10A, so that the angularity (angular maneuverability) in the direction aligned with the longitudinal axis L-L of the plate 10, of a fastener inserted therethrough, is symmetric relative to the thickness axis 16 aligned with the axis of the through hole 12 and perpendicular to the longitudinal axis L-L, and therefore the angular maneuverability is also symmetric in both directions relative to the longitudinal axis L-L.

Figure 4A:
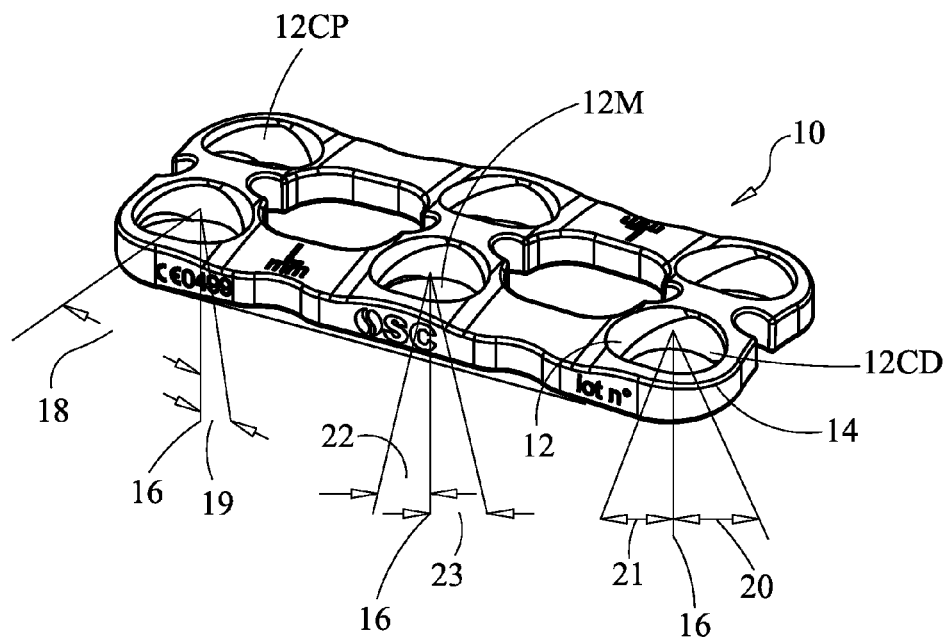
FIG. 4A is a perspective view of the plate of FIG. 3B.
Figure 4B:
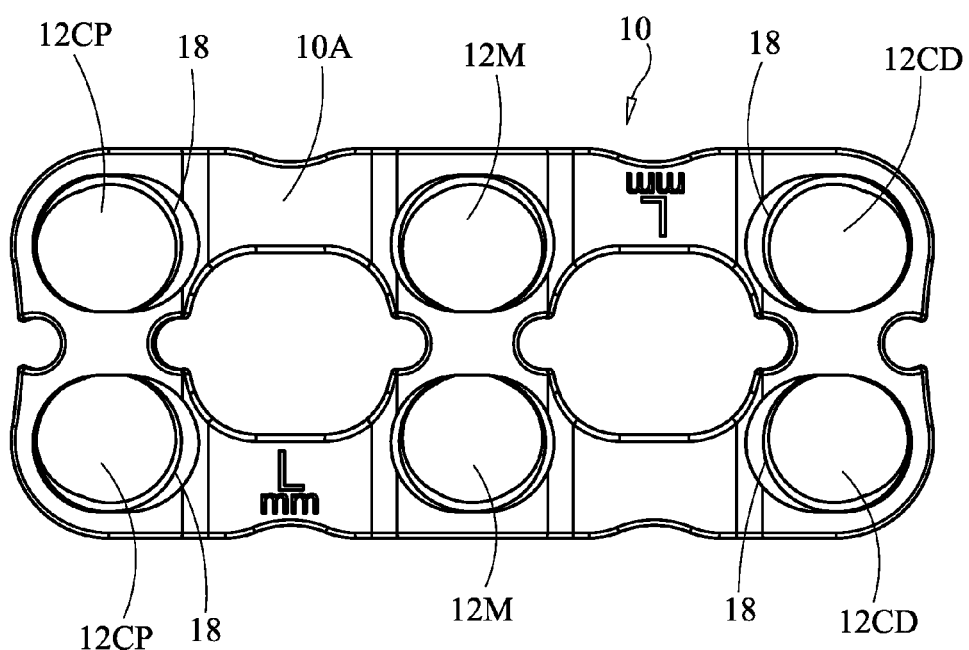
FIG. 4B is a view of the anterior surface of the plate of FIG. 4A.

Thus, for example, in an embodiment having three pairs of circular through holes 12 for use in implanting on the spine, such as illustrated in FIGS. 4A-4B, the circular through holes 12CP located closest to the end of plate to be positioned most cephalad on the spine are inclined 18 on the anterior surface toward the caudal direction. That is, the central axis of the circular through hole 12CP is not perpendicular to the anterior surface of the plate, but is angled toward the caudal direction (to the right in FIGS. 4A-4B) and the circular through holes 12CD located closest to the end of the plate to be positioned most caudal on the spine are inclined 18 toward the cephalad direction on the anterior surface of the plate.

That is, the central axis of the circular through hole 12CD is not perpendicular to the anterior surface of the plate, but is angled toward the cephalad direction (to the left in FIGS. 4A-4B). The intermediately located through holes 12M are not inclined. That is, the central axis of the circular through hole 12M is substantially perpendicular to the anterior surface 10A of the plate. Consequently, fasteners 70 inserted through through holes 12CP can be angled by a maximum cephalad angle 18 (each angle is described relative to the thickness axis 16 and the direction of the angle is the direction toward which the distal tip of the fastener 70 points) that is greater than the maximum caudal angle 19. For example, angle 18 may be from about twenty-live to about thirty-five degrees, typically about thirty degrees, and angle 19 may be from about five to about fifteen degrees, typically about ten degrees. Conversely, fasteners 70 inserted through through holes 12CD can be angled by a maximum caudal angle 20 that is greater than the maximum cephalad angle 21. For example, angle 20 may be from about twenty-five to about thirty-five degrees, typically about thirty degrees, and angle 21 may be from about five to about fifteen degrees, typically about ten degrees. In the embodiment shown in FIG. 4A, angle 18 is equal to angle 20 (although the fasteners 70 point in opposite directions) and angle 19 is equal to angle 21 (although the fasteners 70 point in, opposite directions). Fasteners 70 inserted through the intermediate through holes 12M can be angled by a maximum caudal angle 22 that is equal to the maximum cephalad angle 23. For example, angle 22 may be from about fifteen to twenty-five degrees, typically about twenty degrees, and angle 23 may be from about fifteen to twenty-five degrees, typically about twenty degrees.

FIGS. 5A-5B illustrate end views of the system of FIG. 1 viewed facing the left end of the system of FIG. 1. FIG. 5A shows that the central axis 24 of the through hole 12 is medially inclined relative to the thickness axis 16 that is perpendicular to the transverse axis T-T of the plate 10 (16 is also perpendicular to the longitudinal axis L-L of the plate 10). The through hole 12 (i.e., the through hole on the right in FIG. 5A) is symmetrical with its paired hole relative to the median line and is therefore angled in the opposite direction such that it is angled toward the median. Each pair of through holes may be angled in this manner. The angle 25 between the thickness axis 16 and the hole axis 24 may range from about three degrees to about seven degrees, typically about five degrees. Accordingly, fasteners 70 passed through the holes 12 are angled medially toward their paired fasteners 70. This forms a wedge configuration, such that when the fasteners are installed in bone in these orientations, they trap a wedge of bone 26 between each pair of fasteners 70. This greatly increases the "pullout strength", i.e., the amount of force that is required to pull the fasteners out of the bone, and therefore greatly reduces the occurrence of failure in this regard.

FIG. 6 is a perspective view of a fastener 70 according to an embodiment of the present invention. Fastener 70 may be configured as a variable fastener or a fixed fastener, according to different embodiments of the present invention. The main body portion of the fastener 70 as shown in FIG. 6 is the same, whether the fastener 70 is configured as a variable fastener or a fixed fastener. Fastener 70 includes a threaded shaft 72 having a distal tip 72D and threads 72T that extend over substantially the full length of the shaft 72. The threads 72T may be self-drilling and/or self-tapping for purposes of installation into bone. Fastener 70 includes a head 74 that extends proximally from shaft 72 and has a greater cross-sectional area than that of shaft 72. The length of fastener 72 may vary, primarily due to different embodiments that have different length shafts 72, as head 74 remains substantially unchanged in different length embodiments. Different lengths may be needed depending upon the location of the bone that the fastener is to be installed in, the type of bone, the condition of the bone, differences between patients, and other variables that are known to those of ordinary skill in the art. For example, fasteners may be provided in lengths of 12 mm, 14 mm, 16 mm and 18 mm, although other lengths may also be provided.

The diameter (non-tapered portion) of the shaft 72 may likewise be provided in different sizes. For example, fasteners 70 may be provided with shaft diameters of 4 mm and 4.5 mm, although other diameters may also be provided. Fasteners 70 are typically made of titanium, but may alternatively be made of polyether ether ketone (PEEK), carbon fiber-filled polymers, biodegradable polymers or stainless steel.

Head 74 has a convex external surface that may be spherical in shape and includes a plurality of slots 78 therein and circumferentially spaced about the head 74. The slots 78 each have a relatively wider portion at the top and a relatively narrower portion at the bottom portion thereof (portion nearer the shaft 72). This configuration allows utilization of the slots 78 to drive the fastener 70 by applying torque through slots 78 to drive the threads 72T, and also provides for titration of the amount of the designed inward and outward flex of the head portions 74p. Slots 78 are configured to allow head portions 74p to flex inwardly, as well as outwardly, so as to decrease or increase a diameter of the head 74, respectively. Head 74 defines an interior space 80 configured to receive a fixing insert or variable insert therein, as described in detail below. Cam followers 82 are provided on a plurality (typically all, as shown in FIG. 6) of the portions (i.e., leaflets 74p) of the head 74 defined between slots 78.

Figure 7A:
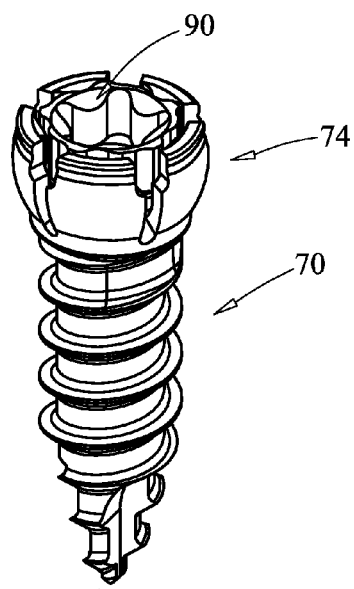
FIG. 7A is a perspective view of a fastener with a variable insert having been installed therein according to an embodiment of the present invention.
Figure 7B:
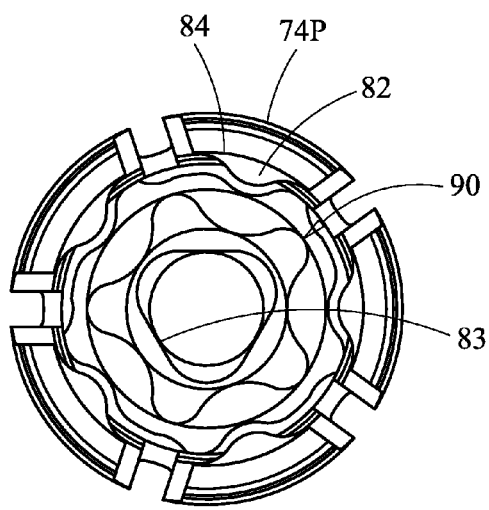
FIG. 7B is a top view of the fastener of FIG. 7A shown in a first configuration according to an embodiment of the present invention.
Figure 7C:
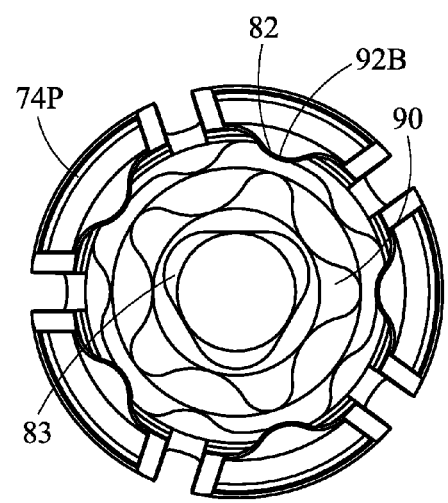
FIG. 7C is a top view of the fastener of FIG. 7A shown in a second configuration according to an embodiment of the present invention.

FIG. 7A shows fastener 70 configured as a variable fastener, as a variable insert 90 having variable cam lobes 92 (see FIG. 9) has been installed in the space 80 of head 74. Variable insert 90 is retained within the space 80 in head 74, but is rotatable relative thereto. In a first configuration, illustrated in the top view of FIG. 7B, variable insert 90 is in a position relative to head 74 such that a clearance gap 84 exists between the variable insert 90 and each cam follower 82. The clearance gaps 84 are sufficient to allow the head leaflets 74p of head 74 to flex radially inwardly to reduce the outside diameter of the head 74 sufficiently to allow it to be passed through the anterior portion of through hole 12 having a first inside diameter, as described in more detail below. The clearance gaps 84 are provided by aligning valleys 94 on variable insert with cam followers 82, as valleys 94 are dimensioned to provide the desired distance of clearance gap 82 (from cam follower 82 to valley 94) to allow head 74 to be inserted through the anterior diameter of the through hole. In a second configuration illustrated in the top view of FIG. 7C, variable insert 90 has been rotated (clockwise, in the configuration shown in FIG. 7C, but could alternatively be configured to rotate counterclockwise to assume this configuration) relative to head 74 in a configuration where leaflets 74p are prevented from flexing inwardly. Initially, during the rotation from the first configuration to the second configuration, the contact surfaces 92a of cam lobes 92 flex the leaflets 74p outwardly slightly as they come in contact with cam followers 82. Upon further rotation, cam followers 82 snap into notches 92b of cam lobes 92. Notches 92b extend radially outwardly by a distance predetermined to contact the cam followers 82 so that there is no gap between each notch 92b and cam follower 82, respectively, as shown in FIG. 7C. Accordingly, head 74 is maintained in it unstressed configuration, where leaflets 74p are neither flexed inwardly nor outwardly. Each notch 82 is flanked on one side by contact surface 92a and on the other side by contact surface 92c of the cam lobe. Contact surface 92a extends further radially outward than notch 82 and contact surface 92c extends even further radially outward than contact surface 92a. Accordingly, cam followers 82 snap into a stable configuration, received by notches 92b and held stably in that configuration by the adjacent cam lobe surfaces 92a, 92c.

Figure 8A:
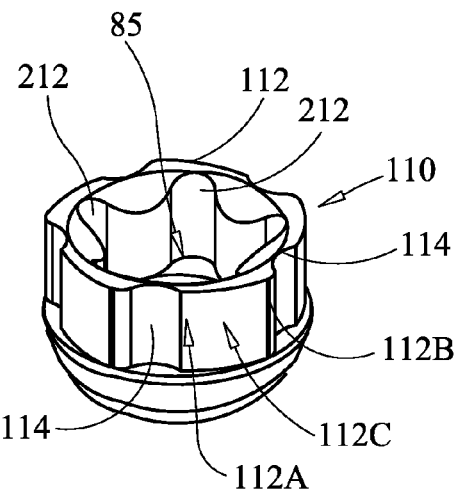
FIG. 8A is a perspective view of a fixing insert according to an embodiment of the present invention.
Figures 8B, 8C:
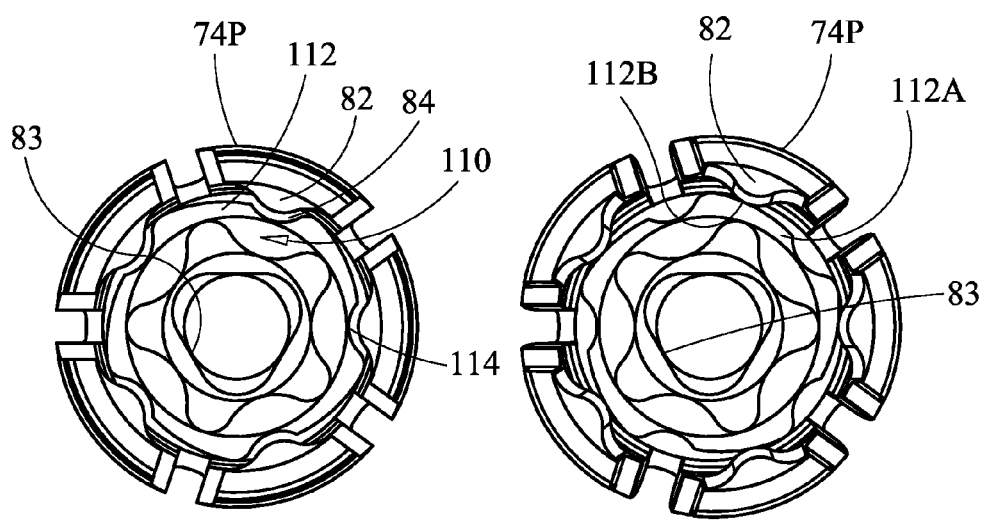
FIG. 8B is a top view of the fixing insert of FIG. 8A having been inserted into a fastener and shown in a first configuration according to an embodiment of the present invention.
FIG. 8C is a top view of the fixing insert of FIG. 8A having been inserted into a fastener and shown in a second configuration according to an embodiment of the present invention.

FIG. 8A illustrates a perspective view of a fixing insert 110 according to an embodiment of the present invention. Like the variable insert 90 illustrated in FIG. 9, fixing insert 110 is configured to be installed in space 80 of head 74 to form a fixed fastener, wherein the fixing insert 110 is retained in head 74 while also being rotatable relative to head 74. Fixing insert 110 has fixing cam lobes 112. Fixing cam lobes have continuously increasing contact surfaces that increase (radial distance from the center of the fixing insert 110) in the amount of radial extension from the initial contact location 112a to the maximum extending location 112b. In a first configuration, shown in FIG. 8B, fixing insert 110 is in a position relative to head 74 such that a clearance gap 84 exists between the fixing insert 110 and each cam follower 82. The clearance gaps 84 are sufficient to allow the head leaflets 74p of head 74 to flex radially inwardly to reduce the outside diameter of the head 74 sufficiently to allow it to be passed through the anterior portion of through hole 12 having a first inside diameter, as described in more detail below. The clearance gaps 84 are provided by aligning valleys 114 on fixing insert 110 with cam followers 82, as valleys 114 are dimensioned to provide the desired distance of clearance gap 82 (from cam follower 82 to valley 114) to allow head 74 to be inserted through the anterior diameter of the through hole. Fixing insert 110 can be rotated (clockwise, in the configuration shown in FIG. 8C, but could alternatively be configured to rotate counterclockwise to assume this configuration) relative to head 74 into a second configuration where cam lobe surfaces 112a initially contact the cam followers 82 and then, as rotation progresses, leaflets 74p are flexed outwardly by the driving forces provided by increasingly pushing the leaflets outwardly as the cam surfaces 112c-112b increasingly extend from the center of the insert 110, at the locations where the cam surfaces 112c-112b contact the cam followers 82 and drive them outwardly.

Figure 10:
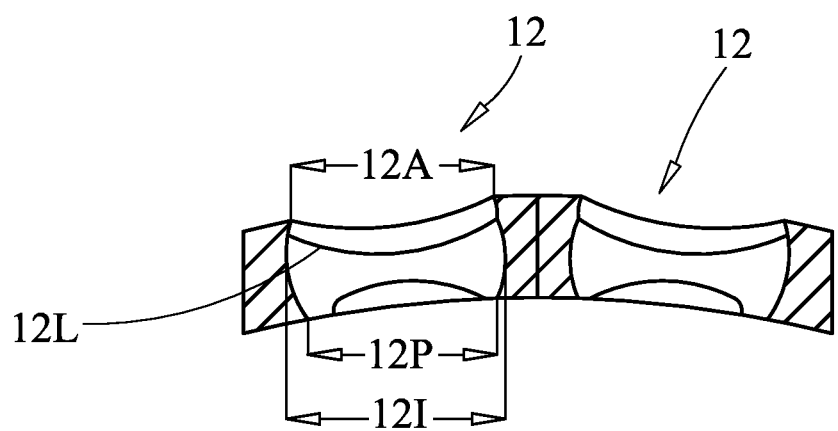
FIG. 10 is a cross-sectional view of a plate taken along line 10T-10T in FIG. 4A.

FIG. 10 is a cross-sectional view of plate 10 taken along line 10T-10T in FIG. 4A. FIG. 10 illustrates that through holes 12 each have a first or anterior diameter 12A, a second or intermediate diameter 121, and a third or posterior diameter 12P. Intermediate diameter 121 is greater than anterior diameter 12A and, typically, anterior diameter 12A is greater than posterior diameter 12P. In one non-limiting embodiment, anterior diameter 12A was about 5.3 mm, intermediate diameter 121 (maximum intermediate diameter, as the wall surfaces in this embodiment were spherical) was about 5.6 mm and posterior diameter 12P was about 4.55 mm. However, these diameters may vary and may be selected from a range, for example, of about 4.8 mm to about 5.8 mm (anterior diameter 12A), of about 5.1 mm to about 6.1 mm (intermediate diameter 121) and of about 4.1 mm to about 5.1 mm (posterior diameter 12P). However, in each embodiment, anterior diameter 12A is always smaller than intermediate diameter 121. A lip 12L is formed at the juncture perimeter between diameters 12A and 121. This lip 12L and the fact that diameter 12A is less than the diameter of the head 74 are what prevent backout of the head 74 once head 74 has been passed through anterior diameter 12A and into intermediate diameter 121.

Regardless of whether a fixed or variable fastener 70 is being installed in opening 12, the first configuration allows flexing of the leaflets 74p. In an unflexed, configuration, the outside diameter of head 74 at its distal end is greater than the anterior diameter 12A of through hole 12. However, when shaft 72 is inserted through opening 12, so as to extend out of the posterior face of plate 10 and head 74 interfaces with the anterior opening of hole 12, as the head 12 is pushed into the opening 12, the walls surrounding the anterior diameter 12A force the leaflets 74p inwardly so that the head diameter becomes slightly less than the anterior diameter 12A and the head 74 enters the intermediate space of the through hole 12 as illustrated in FIGS. 1, 5A and 5B. As the distal end of the head 74 clears the anterior opening of the through hole 12, the intermediate diameter 121 of the through hole 12 allows the leaflets 74p to resiliently return to their unflexed configurations, whereby head 74 returns to its unflexed configuration having an outside diameter at its distal end that is greater than anterior diameter 12A.

At this time, when fastener 70 is a variable fastener, the variable insert 90 is rotated to the second configuration described above and shown in FIG. 7C, wherein notches 92b interface with cam followers 82. In this second configuration, although the variable insert 90 does not cause outward flexing of the leaflets 74p, it does prevent inward flexing of the leaflets 74p. Accordingly the head 74 is thus maintained in its unflexed configuration. In the unflexed configuration, the outside diameter of head 74 is greater than the anterior diameter 12A and thus the fastener 70 is prevented from backing out of the through hole 12 since head 74 cannot pass back through the anterior opening of the hole 12. However, the outside diameter of head 74 in the unflexed configuration is less than the interior diameter 121. Accordingly, head 74 is allowed to articulate (e.g., allowed to angulate in the ranges shown in FIG. 4A) relative to the through hole 12 and plate 10.

When the fastener 70 being inserted is a fixed fastener, the first configuration allows flexing of the leaflets 74p, as noted above. In an unflexed, configuration, the outside diameter of head 74 at its distal end is greater than the anterior diameter 12A of through hole 12. However, when shaft 72 is inserted through opening 12, so as to extend out of the posterior face of plate 10 and head 74 interfaces with the anterior opening of hole 12, as the head 12 is pushed into the opening 12, the walls surrounding the anterior diameter 12A force the leaflets 74p inwardly so that the head diameter becomes slightly less than the anterior diameter 12A and the head 74 enters the intermediate space of the through hole 12 as illustrated in FIGS. 1, 5A and 5B. As the distal end of the head 74 clears the anterior opening of the through hole 12, the intermediate diameter 121 of the through hole 12 allows the leaflets 74p to resiliently return to their unflexed configurations, whereby head 74 returns to its unflexed configuration having an outside diameter at its distal end that is greater than anterior diameter 12A.

At this time, the fastener 70 is oriented angularly relative to plate 10 and through hole 12 as desired, and the fixing insert 110 is rotated to the second configuration described above, wherein the cam surfaces 12c applying continually increasing outward amounts of flexion over travel from 112a-112b against cam followers 82. Thus, the installer can rotate insert 110 to flex the leaflets 74p outwardly to contact and apply compression forces against the inner walls lining the interior portion of the through hole 12. In this way, the installer can establish a desired amount of compression force (which may be predetermined) against the inner walls thereby preventing articulation of head 74 relative to the inner wall, through hole 12 and plate 10. Likewise, the outer diameter of head 74 is greater than anterior diameter 12A and this prevents head 74 9 and fastener 70) from backing out of the through hole 12.

Figure 11A:
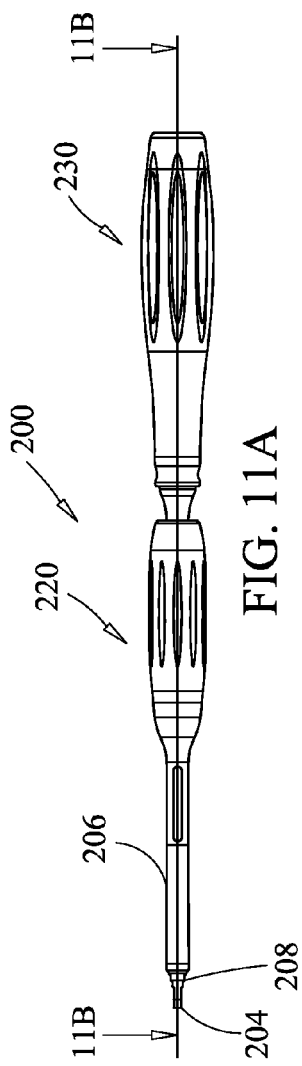
FIG. 11A is a plan view of an instrument for installation of a fastener during a surgical procedure according to an embodiment of the present invention.

FIG. 11A is a plan view of an instrument 200 for installation of a fastener 70 during a surgical procedure to attach plate 10 to bone portions. Instrument 200 includes a first shaft 202 (see FIG. 11B) having a first end effector 204 configured to engage with the fastener 70 to torque the fastener 70 into an intended target, such as by screwing threads 72 into bone for example. End effector 204 is configured to mate with driving feature 83 of fastener 70, there being provided an opening 85 through each of variable insert 90 and fixing insert 10 that allows end effector 204 to pass therethrough and engage driving feature 83 and which allows shaft 202 to rotate relative to insert 90 or 110 to as to allow driving of the threads 72. By viewing the end view of end effector 204 in FIG. 11C and the driving feature 83 in each of FIGS. 7B, 7C, 8B and 8C, it can be seen that the end effector 204 and driving feature 83 in this embodiment are substantially triangular shaped but with rounded corners. It is noted that these features of the present present invention are not limited to this shape, as many other different shape choices could be substituted, so long as end effector 204 mates with driving feature 83 to effect driving of the fastener 70.

Figure 11B:
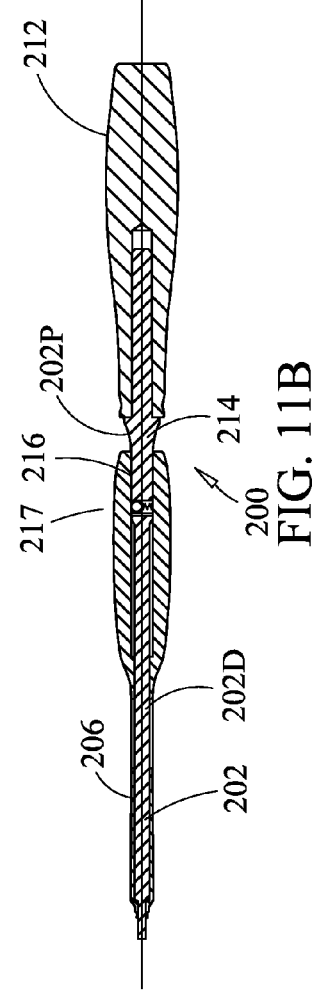
FIG. 11B is a longitudinal sectional view of the instrument of FIG. 11A taken along line 11B-11B.
Figure 11C:
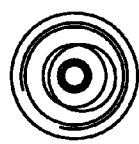
FIG. 11C shows an end view of the end effector of the fastener driver of the instrument of FIG. 11A according to an embodiment of the present invention.

A second shaft 206 (FIG. 11A) is provided coaxial with and rotatable relative to first shaft 202 (see FIG. 11B). The second shaft 206 has a second end effector 208 configured to engage a locking mechanism of the fixing insert 110 as well as the variable insert 90 to torque the locking mechanism and prevent backout of the fastener from the through hole 12 as described above. Additionally, the second shaft 206 is axially slidable relative to the first shaft 202 to allow the second end effector 208 it to be released from or engaged with (depending upon the will of the operator) the fixing insert 110 or variable insert 90 when the first end effector 204 is engaged with the driving feature 83. Optionally, the second shaft 206 may be spring-loaded or otherwise biased toward a distal end of the first shaft so as to default to engaging the second end effector 208 with the insert 90 or 110 when the first end effector 204 is engaged with the driving feature. The operator can then simply slide the shaft/tube 206 back proximally to disengage the end effector 208 from the insert 90, 110 if and when desired.

Figure 9:
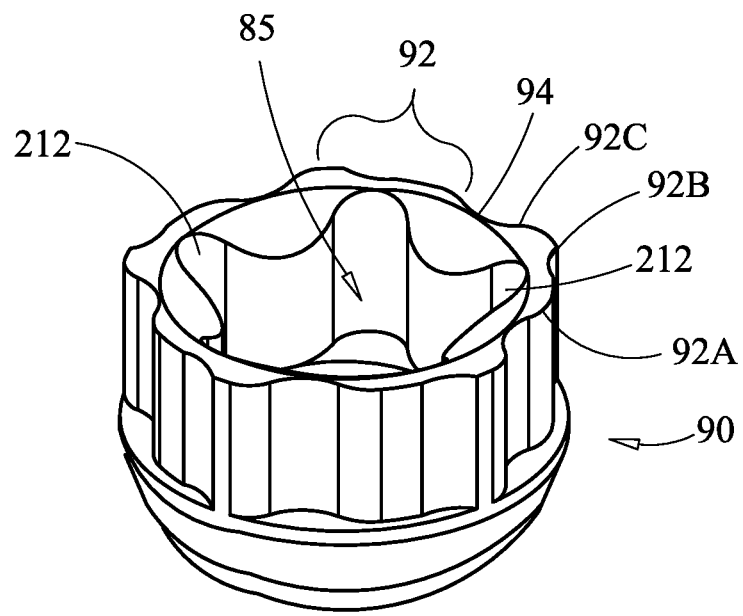
FIG. 9 is a perspective view of a variable insert according to an embodiment of the present invention.

In the embodiment shown, the second end effector 208 includes a plurality of protrusions 210 spaced about a circumference thereof and configured to engage mating receptacles 212 in inserts 90, 110 (see FIGS. 8-9). Although preferred, it is noted that this is only one example of an end effector, and that different patterns, shapes, etc. of features may be provided on end effector 208 as long as inserts 90, 110 are configured with mating features to engage with the end effector. Likewise although a pattern of protrusions equally circumferentially spaced is currently preferred, the present invention is not limited to this pattern or number, as two, three, four or more than five protrusions 210 could be provided. Also, the protrusions 210 need not be equally circumferentially spaced, although that is preferred.

A first handle 212 is fixed to (and may optionally be integral with) the first shaft 202 and is useable to torque the fastener 70 into the intended target, such as by screwing threads 72T, via torque transmitted from handle 212 through shaft 202, end effector 204, driving feature 83 and shaft 72 and to threads 72T. Alternatively, shaft 202 may be segmented with a proximal portion 206P thereof extending distally from handle 212 and being provided with a distal end 214 that mates with a socket 216 provided at a proximal end of the distal portion 202D of shaft 202, as illustrated in FIG. 11B. Ball 217 keeps proximal portion 206P in the retracted or extended position by functioning as a spring driven detent against one or the other of grooves (not shown) positioned in the inner walls of the handle 222 where the annulus is formed to accept shaft 202, at locations to place the distal end of the cam driver in an extended configuration (where it can mate with an insert) or, alternatively, in a retracted position (where it is spaced apart from an insert).

Figure 12A:
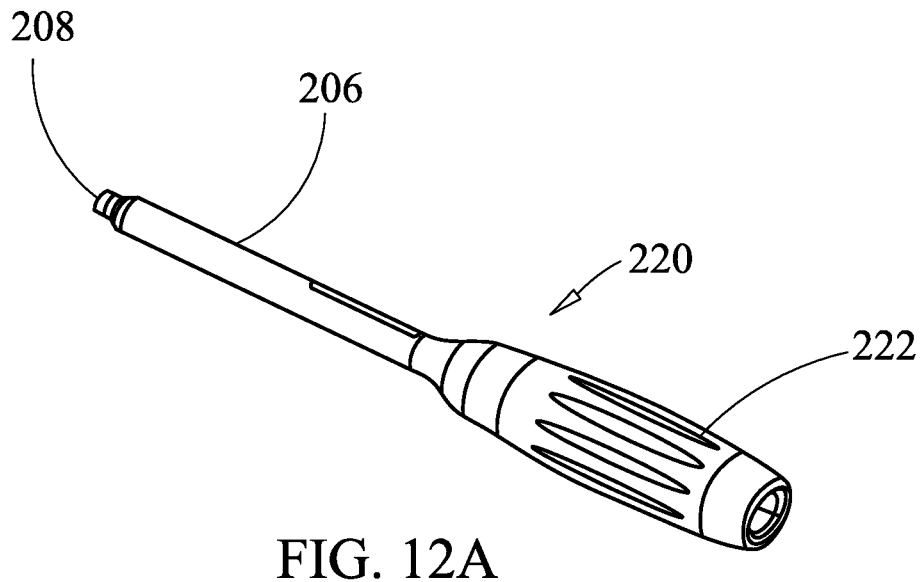
FIG. 12A is a perspective view of a cam driver portion of the instrument of FIG. 11A, having been removed off of the fastener driver portion of the instrument of FIG. 11A, according to an embodiment of the present invention.
Figure 12B:
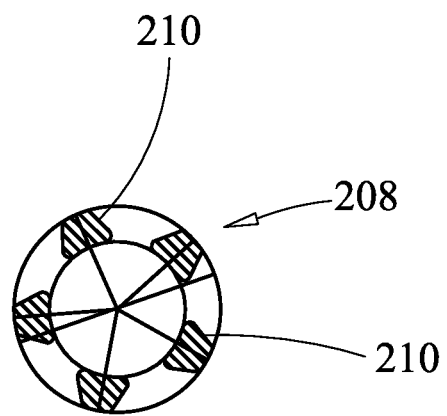
FIG. 12B shows an end view of the end effector of the cam driver of FIG. 12A.

FIG. 12A is a perspective view of the cam driver 220 portion of instrument 200 have been removed off of the fastener driver 230 portion of instrument 200. Although the portions 220, 230 can be used separately and are used separately under certain conditions, they are typically used together in assembled form as shown in FIGS. 11A-11B. Cam driver 220 includes a second handle 222 fixed to second shall (tube) 206, which is useable to torque the locking mechanism, by transferring torque through handle 222, shaft/tube 206, end effector 208 to mating receptacles 212 to rotate insert 90 or 110 relative to head 74 in a manner as described above. Note that one or both of handles 212, 222 have been provided with indents, neutrally, or other features to enhance the grip of the user as the handle is torqued.

Figure 13:
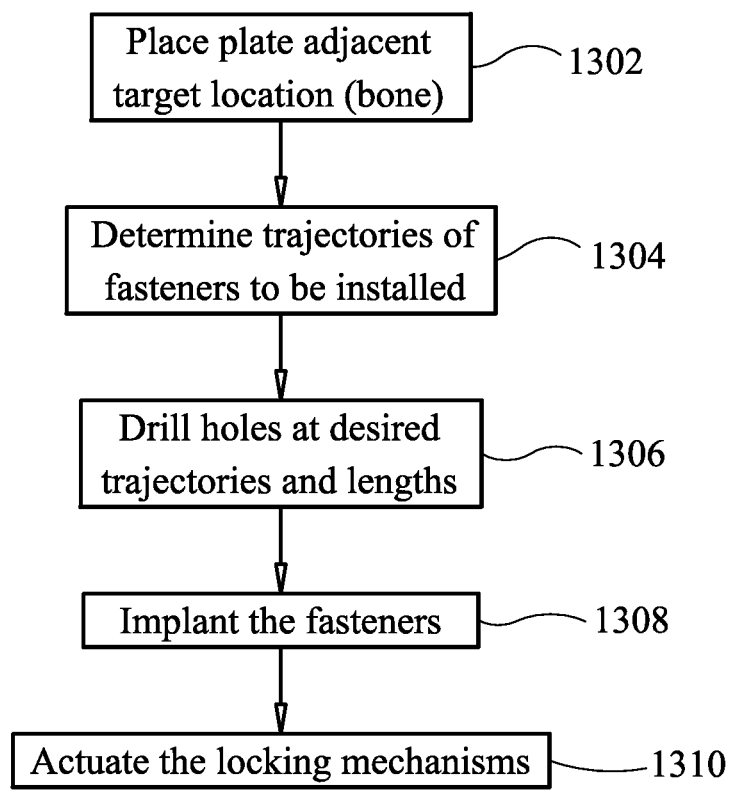
FIG. 13 illustrates events that are carried out during a method of installation of a surgical plate system according to an embodiment of the present invention.

FIG. 13 illustrates events that are carried out during a method of installation of a surgical plate system according to an embodiment of the present invention. After preparation of the patient using standard, accepted surgical techniques to expose the surgical site (vertebrae or bone portions) and determining the appropriate size plate 10 to be implanted, the plate is placed adjacent the target bone location at event 1302. At event 1304, the surgeon determines the trajectories along with the fasteners 70 will be implanted. Fluoroscopy may be used to assist in making these determinations. Care should be taken so that the trajectories do not intersect with nerve locations, vascular tissues, or exit the bone along any portion of the trajectories.

Once the trajectories have been determined and the lengths and shaft diameters of the fasteners 70 to be implanted have been determined, holes are drilled through the through holes 12 and into the bone at the determined trajectories and depths, using drill bits that correspond to the determined shaft diameters and fastener lengths. Next the fasteners 70 are implanted into the bone(s) at event 1308. To implant the fasteners, the instrument 200 is manipulated to at least engage the first end effector 204 with the driving feature 83 (e.g., surfaces of a socket that mates with the end effector 204). In embodiments where instrument 220 is biased toward the distal end of assembly 200, end effector 208 will also engage with mating receptacles 212 of the insert 90 or 110 contained in the fastener to be implanted. In non-biased embodiments, the end effector 208 may be retracted and need not be engaged with the insert at this time. However, by having the insert engaged by end effector 208 at this time, this will increase the self-retaining capability of the end effector 204, that is the ability to retain the fastener 70 thereon prior to engaging it in the target. Next, the fastener 70 is inserted, tip first, through a predetermined through hole 12 and handle 230 is torqued to screw fastener 70 into the bone as screw threads 72 tap/drill their way along the drill hole trajectory formed earlier. The fastener 70 is not completely tightened until all fasteners 70 have been implanted by this same technique, and then the surgeon can go back and completely tighten each fastener to the desired amount of torque. One the distal end of a fastener head 74 is received within the intermediate diameter portion 121 of the through hole 12, then the leaflets 74p return to their unflexed configurations so that head 74 has a larger outside diameter at its distal end than the anterior diameter 12A/lip 12L, as noted in detail above.

Once all fasteners 70 have been torqued into the bone at the desired amounts of torque, instrument 200 is next used to actuate the inserts to transition them from the first configuration to the second configuration. In embodiments where the second shaft 206 is distally biased, the end effector 208 will have already been engaged with mating receptacles 212. In unbiased embodiments, the surgeon will at this time slide instrument 220 distally over shaft 202 to engage the second end effector 298 with the mating receptacles 212 of the insert 90, 110. Then, handle 220 is torqued in a first rotational direction (typically clockwise, although an embodiment with left handed threads could be provided for torqueing counter-clockwise, in which case threads 72T would also typically be made to be left handed), while the relative rotational position of threads 72T relative to the bone in which they are implanted is maintained stationary, which may require application of counter-torque (i.e., torque in the opposite rotation direction to that applied via handle 222) via handle 212. As noted above, if the insert is a variable insert 90, this movement to the second configuration locks the head 74 in the sense that it prevents leaflets 74p from flexing inwardly, thereby preventing backout of the head through the anterior surface/collar of the through hole 12. If the insert is a fixing insert 110, then torqueing of the insert 110 is performed to the extent that the head 74 applies compression forces to the inner walls defining the through hole and therefore head 74 becomes fixed relative to the through hole 12 and plate, thereby fixing the trajectory/angle of the fastener 70 relative to the plate 10. In the case of the variable fastener 70, head 74 is prevented from backing out of the through hole 12, but head 74 can still articulate relative to the through hole 12 when in the second configuration, so that the trajectory/angle of variable fastener 70 relative to the plate 10 can change. Once the locking mechanism of all screws have been successfully actuated to place the inserts 90,110 in the second configurations, the implantation of system 100 is complete and standard surgical procedures can be used to close the patient. In the embodiment shown in FIG. 1, variable fasteners 70 having variable inserts 90 were used in all four end holes 12 and fixed fasteners having fixing inserts 110 were used in the two intermediate through holes 12. As noted above, the present invention is not limited to this arrangement as either a fixed or a variable fastener can be used in any of the through holes 12, according to the surgeon's preference.

In one embodiment, where plate 10 is an anterior cervical plate used for implantation on the anterior portions of cervical vertebrae, the usual position of a patient for an anterior cervical approach was used. Disc excision and spinal decompression were performed using standard surgical techniques. Appropriate allografts were inserted between the cervical vertebrae where disc excision was performed. Care was taken to perform appropriate soft tissue dissection and neural elements decompression. Anterior osteophytes were carefully removed to optimize the bone-plate interface. During event 1306, the two most cranial holes were drilled first. An awl was used to first breach the bone cortex. A drill bit was used that corresponds with the planned length of the fastener to be used. The bit can be operated either by power drill or hand drill. The drill is operated until it advances to a depth where a stopper provided on the drill contacts the bone. Intervertebral implants, such as cages may be inserted between the vertebrae where a discectomy was performed. Care should be taken not to over-compress the disc levels as this may result in delayed subsidence of the implants into the vertebral bodies.

When choosing a suitable plate 10 size it must be considered that the intervertebral discs in the cervical spine are slightly inclined from anterocaudal to posterocranial. Plates 10 may be provided in pre-lordosed (bent) shape, but the lordosis may be increased or decreased by further bending with a plate bending clamp, not shown. The fasteners 70 may be color-coded for diameter, length, and whether they are equipped with a variable insert 90 or a fixing insert 110.

Fasteners 70 are provided to the surgeon with one or the other of a variable insert 90 or a fixing insert 110 already pre-installed. As noted earlier, plates 10 can be installed with all fixed fasteners 70, all variable fasteners 70, or any combination of the two. Fasteners 70 have a shaft diameter of 4.0 mm are typically used, but 4.5 mm fasteners or larger may be used when needed, such as when the bone has been stripped and a larger diameter thread is needed.

The variability provided by variable fasteners 70 allows for variation in trajectory to accommodate for patient anatomical differences. Also, the continued variability after implantation accommodates subsidence and allows for the desired load-sharing between the system 100 and the spine, which in turn provides ideal loading of any graft that may be placed between adjacent vertebrae, such as required for optimal fusion. Once locked (i.e., once insert 90 has been rotated to the second configuration), the variable fastener retains the ability to pivot along the sagittal plane to allow for subsidence. Once locked (i.e., once insert 110 has been torqued to compress head 74 against the inner walls defining the through hole 12), the fixed fastener cannot move and thereby maintains the initial intended angle of the fastener 70 relative to the plate 10. The order of implantation of the fasteners, in one embodiment, was to first implant a fastener 70 through one of the most cephalad through holes 12, followed by implanting a fastener 70 through the most caudal through hole diagonal to the first implanted fastener. After that the rest of the fasteners 70 should be implanted symmetrically, as this minimizes movement from the intended location of the plate 10 as placed.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A surgical plate system, said system comprising:
    a plate having an anterior surface, a posterior surface, side surfaces substantially perpendicular to portions of said anterior surface joined by said side surfaces, a longitudinal axis, and a transverse axis;
    wherein said plate comprises a pair of openings-arranged side by side along a direction of said transverse axis extending through said anterior and posterior surfaces; a first opening of said pair having a first axis defining a direction in which said first opening extends from said anterior face to said posterior face, and a second opening of said pair having a second axis defining a direction in which said second opening extends from said anterior face to said posterior face, wherein said first and second axes are medially inclined towards one another and angled relative to said respective side surfaces, such that said first and second axes converge toward one another in a direction from said anterior surface to said posterior surface;
    a variable fastener configured and dimensioned to connect to said plate, said variable fastener comprising a first head and a first shaft extending distally from said first head, wherein said first head is configured to assume different proximal end diameters, wherein said first head, in a first configuration allows inward flexing to reduce a diameter of said first head to allow said first head to pass through a first entrance opening of said first opening, and wherein in a second configuration, said first head is prevented from flexing inwardly thereby preventing said first head from backing out of said first entrance opening, while allowing articulation of said first head, within said first opening, relative to said plate, and wherein a trajectory angle of said variable fastener can change relative to said plate even after said variable fastener has been torqued into a bone and upon completion of installation of said fastener and plate, and wherein said variable fastener is provided with a variable cam that interacts with a protrusion on an inner surface of said head, said variable cam including a notch in a cam surface of said variable cam configured to mate with said protrusion, wherein in said first configuration, said protrusion is separated from a portion of said cam by a first distance that allows said inward flexing sufficient to reduce said diameter of said head to allow said head to pass through said first entrance opening of said first opening, and wherein in said second configuration, said protrusion of said head snaps into said notch, thereby preventing said head from flexing inwardly and preventing said head from backing out of said first entrance opening, wherein, in said second configuration, said head is maintained in an unstressed configuration, where said head is neither flexed inwardly nor outwardly; and
    a fixed fastener configured and dimensioned to connect to said plate, said fixed fastener comprising a second head and a second shaft extending distally from said second head, wherein said second head is configured to assume different proximal end diameters, and wherein said second head, in a first configuration allows inward flexing to reduce a diameter of said second head to allow said second head to pass through a second entrance opening of said second opening, and wherein in a second configuration, said second head is flexed outwardly, thereby preventing said second head from backing out of said second entrance opening and also compressing said second head against inner side walls of said plate surrounding said second opening, thereby preventing articulation of said second head, within said second opening, relative to said plate.

2. The system of claim 1, wherein said first through hole is formed nearer a first end of said plate, said system further comprising a third opening formed nearer a second end of said plate, wherein, in an undeformed configuration of said plate, said first opening comprises a first substantially spherical central portion and a first oblong anterior portion, wherein said first oblong anterior portion extends further in a direction away from said first end than in a direction toward said first end, relative to a central axis of said first opening so as to allow angulation of said fastener relative to a perpendicular to the longitudinal axis in a direction from said anterior surface to said posterior surface, by a first maximum angle toward said first end, and by a second maximum angle toward said second end, wherein said first maximum angle is greater than said second maximum angle.

3. The system of claim 2, wherein said third opening comprises a second substantially spherical central portion and a second oblong anterior portion, wherein, in an undeformed configuration of said plate, said second oblong anterior portion extends further in a direction away from said second end than in a direction toward said second end, relative to a central axis of said third opening so as to allow angulation of said fastener relative to said perpendicular to said longitudinal axis in a direction from said anterior surface to said posterior surface, by a third maximum angle toward said second end, and by a fourth maximum angle toward said first end, wherein said third maximum angle is greater than said fourth maximum angle.

4. The system of claim 2, further comprising a fourth opening formed intermediate of said first and third openings along a direction of the longitudinal axis;
   wherein said fourth opening is configured to allow angulation of said fastener relative to said perpendicular to the longitudinal axis in a direction from said anterior surface to said posterior surface, by a third maximum angle toward said first end, and by a fourth maximum angle toward said second end, wherein said third and fourth maximum angles are substantially equal, wherein said first maximum angle is greater than said third maximum angle, and wherein said second maximum angle is less than said fourth maximum angle.

5. The system of claim 1, wherein said fixed fastener is provided with a fixing cam that interacts with a protrusion on an inner surface of said second head, wherein in said first configuration, said protrusion is separated from a portion of said fixing cam by a first distance that allows said inward flexing sufficient to reduce said diameter of said second head to allow said second head to pass through said second entrance opening of said second opening, and wherein said fixing cam has a lobe with a progressively increasing radius, whereby rotation of said fixing cam engages said lobe with said protrusion of said second head, wherein a first contact location of said lobe with said protrusion prevents inward flexing of said second head but does not expand said second head and, with increasing rotation of said cam, contact of said cam surface with progressively increasing radius flexes said head outward to compress against the inner walls of said through hole, thereby preventing said articulation, wherein said progressively increasing radius of said cam enables variability in an amount of compression force of said head against the inner walls of said second opening.

6. The system of claim 1, wherein said first entrance opening has a first diameter defined by said first opening in said anterior surface, said first opening further comprising a first exit opening having a second diameter defined by said first opening in said posterior surface, and said first opening having a third diameter intermediate of said first entrance opening and said first exit opening, wherein said third diameter is greater than said first diameter.

7. The system of claim 1, wherein, when in said second configuration, an outside diameter of said first head is less than an inside diameter of said through hole in which said first head is received.

8. A surgical plate system, said system comprising:
   a plate having an anterior surface, a posterior surface, a longitudinal axis, a transverse axis and first and second through holes passing through said anterior and posterior surfaces;
   a first entrance opening having a first diameter defined by said first through hole in said anterior surface, a first exit opening having a second diameter defined by said first through hole in said posterior surface, and said first through hole having a third diameter intermediate of said first entrance and first exit openings, wherein said third diameter is greater than said first diameter;
   a second entrance opening having a fourth diameter defined by said second through hole in said anterior surface, a second exit opening having a fifth diameter defined by said second through hole in said posterior surface, and said second through hole having a sixth diameter intermediate of said second entrance and second exit openings, wherein said sixth diameter is greater than said fourth diameter;
   a first fastener configured and dimensioned to connect to said plate, said fastener comprising a first head and a first shaft integral with and extending distally from said first head, wherein said first head is configured to assume different proximal end diameters, and wherein said first head, in a first configuration allows inward flexing to reduce a diameter of said first head to allow said first head to pass through said first entrance opening, and wherein in a second configuration, said first head is prevented from flexing inwardly thereby preventing said first head from backing out of said first entrance opening, wherein said first fastener is a variable fastener comprising a variable cam inserted in said first head, and wherein in said second configuration, said first head is allowed to articulate within said first through hole, relative to said plate, and wherein said variable fastener is provided with a variable cam that interacts with a protrusion on an inner surface of said head, said variable cam including a notch in a cam surface of said variable cam configured to mate with said protrusion, wherein in said first configuration, said protrusion is separated from a portion of said cam by a first distance that allows said inward flexing sufficient to reduce said diameter of said head to allow said head to pass through said first entrance opening of said first through hole, and wherein in said second configuration, said protrusion of said head snaps into said notch, thereby preventing said head from flexing inwardly and preventing said head from backing out of said first entrance opening, wherein, in said second configuration, said head is maintained in an unstressed configuration, where said head is neither flexed inwardly nor outwardly; and
   a second fastener, wherein said second fastener is a fixed fastener comprising a fixing cam inserted in a second head, and a second shaft integral with said second head, wherein said second head is configured to assume different proximal end diameters, and wherein said fixing cam interacts with a protrusion on an inner surface of said second head, wherein in said first configuration, said protrusion is separated from a portion of said fixing cam by a first distance that allows said inward flexing sufficient to reduce said diameter of said second head to allow said second head to pass through said second entrance opening of said second through hole, and wherein said fixing cam has a lobe with a progressively increasing radius, whereby rotation of said fixing cam engages said lobe with said protrusion of said second head, wherein a first contact location of said lobe with said protrusion prevents inward flexing of said second head but does not expand said second head and, with increasing rotation of said cam, contact of said cam surface with progressively increasing radius flexes said head outward to compress against the inner walls of said through hole, thereby preventing said articulation, wherein said progressively increasing radius of said cam enables variability in an amount of compression force of said head against the inner walls of said through hole.

9. The system of claim 8, wherein when said variable fastener is in said second configuration, a trajectory angle of said variable fastener can change relative to said plate, while installed, even after said variable fastener has been torqued into a bone and upon completion of installation of said fastener and plate.

10. The system of claim 8, wherein said plate comprises a third opening arranged side by side with one of said first and second openings to form a pair of openings along a direction of said transverse axis; a first opening of said pair having a first axis defining a direction in which said first opening extends from said anterior face to said posterior face, and a second opening of said pair having a second axis defining a direction in which said second opening extends from said anterior face to said posterior face, wherein said first and second axes are medially inclined towards one another, such that said first and second axes converge toward one another in a direction from said anterior surface to said posterior surface.

11. The system of claim 8, wherein said first opening is formed nearer a first end of said plate, and said second opening is formed nearer a second end of said plate, wherein said first opening is configured to allow angulation of said first or second fastener relative to a perpendicular to the longitudinal axis in a direction from said anterior surface to said posterior surface, by a first maximum angle toward said first end, and by a second maximum angle toward said second end, wherein said first maximum angle is greater than said second maximum angle.

12. The system of claim 11, wherein said second opening is configured to allow angulation of said first or second fastener relative to said perpendicular to said longitudinal axis in a direction from said anterior surface to said posterior surface, by a third maximum angle toward said second end, and by a fourth maximum angle toward said first end, wherein said third maximum angle is greater than said fourth maximum angle.

13. The system of claim 11, further comprising a third opening formed intermediate of said first and second openings along a direction of the longitudinal axis;

wherein said third opening is configured to allow angulation of said first or second fastener relative to said perpendicular to the longitudinal axis in a direction from said anterior surface to said posterior surface, by a third maximum angle toward said first end, and by a fourth maximum angle toward said second end, wherein said third and fourth maximum angles are substantially equal, wherein said first maximum angle is greater than said third maximum angle, and wherein said second maximum angle is less than said fourth maximum angle.

14. A surgical plate system, said system comprising:

a plate having an anterior surface, a posterior surface, a longitudinal axis, a transverse axis and a through hole passing through said anterior and posterior surfaces;

an entrance opening having a first diameter defined by said through hole in said anterior surface, an exit opening having a second diameter defined by said through hole in said posterior surface, and said through hole having a third diameter intermediate of said entrance and exit openings, wherein said third diameter is greater than said first diameter, wherein said through hole is asymmetrically configured to allow angulation of a fastener relative to a central axis of said through hole, in a direction from said anterior surface to said posterior surface, by a first maximum angle toward a first end of said plate, and by a second maximum angle toward a second end of said plate, wherein said first maximum angle is greater than said second maximum angle;

wherein said central axis is angled medially inwardly from an axis perpendicular to said posterior surface in a location immediately surrounding said exit opening; and wherein said fastener is configured and dimensioned to connect to said plate, said fastener comprising a head and a shaft integral with and extending distally from said head, wherein said head is configured to assume different proximal end diameters, and wherein said head, in a first configuration allows inward flexing to reduce a diameter of said head to allow said head to pass through said entrance opening, and wherein in a second configuration, said head is prevented from flexing inwardly thereby preventing said head from backing out of said entrance opening, and wherein said fastener is a variable fastener provided with a variable cam that interacts with a protrusion on an inner surface of said head, said variable cam including a notch in a cam surface of said variable cam configured to mate with said protrusion, wherein in said first configuration, said protrusion is separated from a portion of said cam by a first distance that allows said inward flexing sufficient to reduce said diameter of said head to allow said head to pass through said entrance opening of said first through hole, and wherein in said second configuration, said protrusion of said head snaps into said notch, thereby preventing said head from flexing inwardly and preventing said head from backing out of said entrance opening, wherein, in said second configuration, said head is maintained in an unstressed configuration, where said head is neither flexed inwardly nor outwardly.

\* \* \* \* \*